United States Patent [19]

Heyman

[11] 4,411,267
[45] Oct. 25, 1983

[54] TELEMETRY TRANSMITTER HOLDER

[76] Inventor: Arnold M. Heyman, 2701 West Alameda Ave., Burbank, Calif. 91505

[21] Appl. No.: 237,520

[22] Filed: Feb. 23, 1981

[51] Int. Cl.³ .......................... A61F 7/00; A61N 1/22
[52] U.S. Cl. .................................. 128/385; 128/402; 128/403
[58] Field of Search ............... 128/677, 670, 672, 644, 128/630, 637, 686, 327, 402, 384–385, 387–389, 783, 798, 399, 403; 2/312, 314, 319, 322, 338

[56] References Cited

U.S. PATENT DOCUMENTS

| | | | |
|---|---|---|---|
| 454,313 | 6/1891 | Webb | 128/385 X |
| 501,849 | 7/1893 | Standish | 128/387 |
| 2,288,745 | 7/1942 | Sammis | 128/403 X |
| 2,339,239 | 1/1944 | Carmichael | 2/314 |
| 2,590,212 | 3/1952 | Samuels | 128/387 X |
| 3,407,818 | 10/1968 | Costanzo | 128/384 |
| 3,500,014 | 3/1970 | Longo | 128/402 X |
| 3,659,592 | 5/1972 | Natkanski | 128/686 |
| 3,882,867 | 5/1975 | Moran | 128/402 X |
| 4,026,278 | 5/1977 | Ricketts et al. | 128/644 |
| 4,090,504 | 5/1978 | Nathan | 128/670 |
| 4,092,982 | 6/1978 | Salem | 128/402 X |

*Primary Examiner*—Lee S. Cohen
*Assistant Examiner*—Angela D. Sykes
*Attorney, Agent, or Firm*—Spensley, Horn, Jubas & Lubitz

[57] ABSTRACT

A device having special utility for comfortably holding and protecting medically related telemetry transmitters such as are used to monitor the vital signs of medical patients is described. The device comprises a generally flat closable pouch into which may be placed the telemetry transmitter. Integral with the pouch is a padded strip which secures the pouch about the midsection of the patient beneath his or her hospital gown or other clothing. The device uses Velcro type fastening surfaces and is completely machine washable.

8 Claims, 5 Drawing Figures

U.S. Patent      Oct. 25, 1983      4,411,267
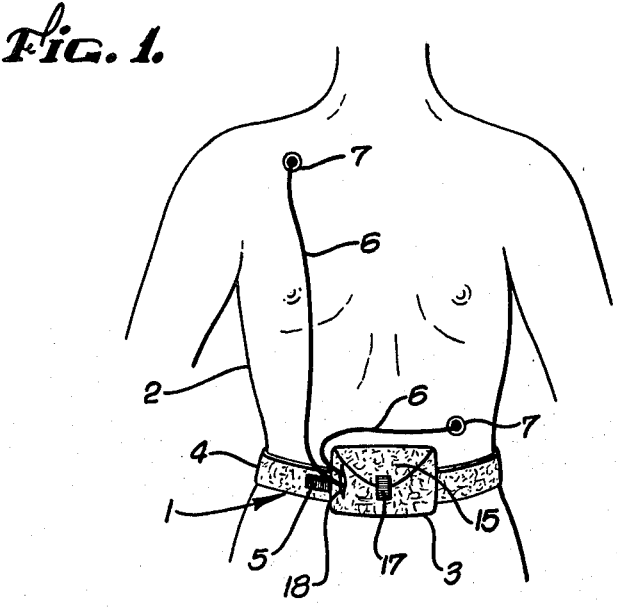
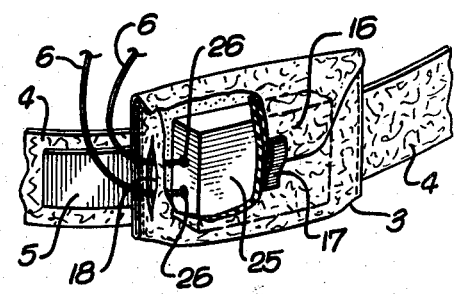
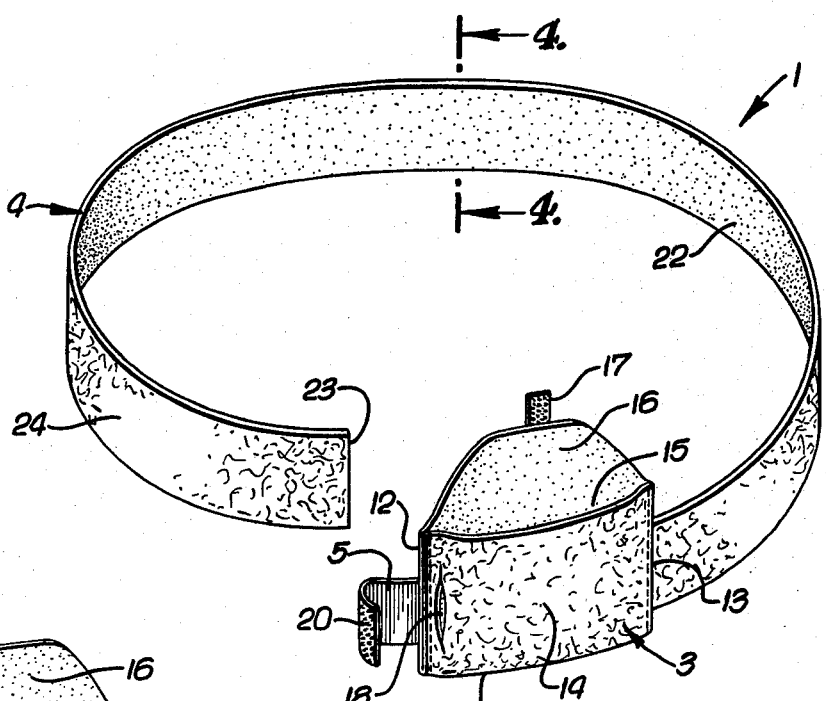
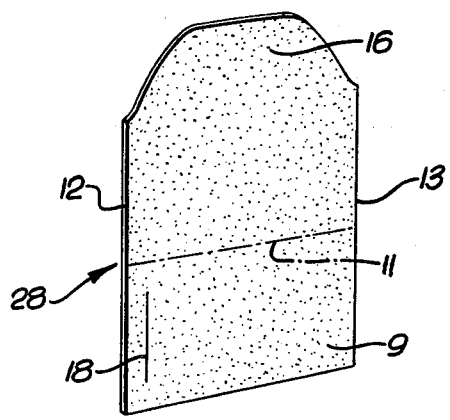
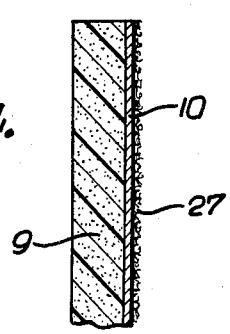

TELEMETRY TRANSMITTER HOLDER

BACKGROUND OF THE INVENTION

1. Field of the Invention

This invention relates to the field of medical devices, and more particularly, to a device which enables a medical patient to securely and comfortably carry about medical equipment, such as a telemetry transmitter used in the monitoring of the vital signs of a medical patient.

2. Prior Art

The combination of electronics and medicine has made it possible for a number of medical patients to have their vital signs continuously monitored following the treatment of a medical problem or diagnosis of a medical condition without the need of being attached to stationary monitoring equipment. Special sensors have been developed which are particularly suitable for detecting the various vital signs of human beings. The signals from these sensors can be coupled to telemetry transmitters, which are small radio transmitters (approximately the size of a pack of cigarettes) that are carried by the patients and which transmit the information concerning the patients' vital signs to receivers placed typically in central locations where the transmitted signals, and hence the patients' vital signs, can be appropriately monitored. The sensors are usually attached to appropriate positions on the body and connected to the transmitter by means of wire leads. A telemetry transmitter, thus, should remain with the patient at all times in order that the vital signs be continuously monitored.

Typically, therefore, the transmitter has been placed either in a pocket of the hospital gown worn by the patient or in a pouch attached to the gown with the wire leads being passed over the neckline of the gown to the sensors. It has been found by many patients that carrying the transmitter in such a manner is neither safe, comfortable nor convenient.

For example, when the transmitter is placed in the pocket of the hospital gown, it has a tendency to fall out of the pocket when the patient bends over. Furthermore, when placed in the breast pocket of the gown, the transmitter, which although approximately the size of a pack of cigarettes, weighs considerably more, tends to exert a downward pull on the gown on the side on which the transmitter is placed, as is typical when a heavy object is placed in a breast pocket. The patient may experience some discomfort from this pull.

Other inconvenience results from having to remove the telemetry transmitter from the hospital gown when the patient changes gowns or is bathed.

In addition to the above-indicated inconveniences and annoyances resulting from attaching the transmitter to the patient's clothing, the patient faces the risk of damage to or malfunctioning of the transmitter and its associated wires and sensors.

A telemetry transmitter attached to loose fitting apparel such as a hospital gown tends naturally to gravitate during the course of a night toward the bed even while staying attached to the clothing, as the patient shifts positions. This may result in the wire leads or sensors becoming disconnected or, if the patient inadvertently rolls over upon the transmitter, discomfort to the patient or damage to the transmitter.

Damage may also result from the transmitter falling out of the patient's pocket. The possible damage that could result from a fall includes damage to the transmitter itself as well as the disconnecting or breaking of the wire leads connecting the sensors to the transmitter.

Also, the transmitter is typically relatively unprotected by the prior art methods from every day accidental impacts with external objects or from accidental exposure to spilled liquids, such as water, which may wet the electrical connections causing a malfunction. Any of these events could result in actual physical damage to the transmitter itself necessitating repair or replacement.

A further very real possibility of damage exists in that the wires leading from the sensors beneath the clothing to a transmitter which has been placed in a pocket may become snagged by protrusions. Such an incident may dislodge the sensor, disconnect or break the wire leads, or even damage the transmitter itself. Thus, not only are patients inconvenienced by the standard techniques for carrying telemetry transmitters, but the patients' lives may be threatened by the disruption of the monitoring of the vital signs resulting from the above described possible events.

Prior to the present invention, patients have also generally not been satisfied with techniques for mounting the telemetry transmitters beneath the clothing. It has been found that the straps and harnesses which have been adapted to carry telemetry transmitters beneath the clothing but have not really been designed for that purpose are uncomfortable.

The present invention overcomes all these problems associated with prior art devices by providing a closable padded pouch for the telemetry transmitter, thus protecting it from damage. The pouch is held in place by a fully adjustable strap made of foam padding. The present invention is especially suitable for being comfortably worn beneath the clothing around the midsection of the body. Thus not only are the transmitter and the wire leads to the sensors fully protected from the hazards associated with the prior art methods and devices, but the patient's freedom is greatly enhanced since now the sensors, wire leads and the transmitter can all be placed beneath the clothing. Moreover, the patient can sleep without any fear that the transmitter will be accidentally dislodged. The present invention provides all these advantages in a device which can be made of materials that are inexpensive, durable, and fully machine washable.

BRIEF SUMMARY OF THE INVENTION

A belt and pouch arrangement particularly suited for holding a medical device, such as a a medically related telemetry transmitter used to monitor the vital signs of medical patients is described. The device is comprised of a closable pouch and a strap, both of which are made of inexpensive and washable material, and is particularly suited for being worn beneath the clothing about the mid-section. The pouch is generally rectangular and flat with an opening along one of the long sides. The telemetry transmitter can be inserted into the pouch through this opening. Along one side of the opening, the pouch extends to form a flap which can be folded over the opening and attached to the pouch so as to hold the telemetry transmitter firmly in place within the pouch. A strap integrally connected at one end of the pouch can be wrapped about the midsection of the patient to hold the pouch in place. The surface of the strap can selectively engage a hook fiber tab attached to the pouch so that the pouch may be secured around the patient's midsection by the engagement of these surfaces.

The problems associated with prior art methods and devices are overcome by this invention. The padded pouch minimizes the possible damage that could result to the telemetry transmitter from inadvertent collisions with external objects and its integral flap assures that the telemetry transmitter will not accidentally be knocked to the ground. Because the wire leads can now be placed entirely beneath the clothing, the chance of their being snagged by external objects and disconnected is completely eliminated.

One object of the present invention, therefore, is to provide a device which can comfortably and safely hold a medical device to a monitored medical patient beneath that patient's clothing.

Another object of the present invention is to provide a means for protecting electronic medical devices from environmental hazards such as impacts or spilled liquids which could damage the devices or cause them to malfunction. The present invention therefore provides a padded waterproof pouch for protecting medical devices from such hazards.

Still aother object of the present invention is to provide a device performing all these functions which is inexpensive, durable and machine washable.

The novel features which are believed to be characteristic of the invention, both as to its organization and method of operation together with further objectives and advantages thereof will be better understood from the following description, considered in connection with the accompanying drawings, in which a presently preferred embodiment of the invention is illustrated by way of example. It is expressly understood, however, that the drawings are for the purpose of illustration and description only, and are not intended as a definition of the limits of the invention.

BRIEF DESCRIPTION OF THE DRAWINGS

FIG. 1 is a view of the device, as it might typically be used, placed in position around the midsection of a person;

FIG. 2 is a cutaway view showing the deployment of a telemetry transmitter within the pouch of the present invention;

FIG. 3 is a perspective view showing the device of the present invention in its preferred embodiment;

FIG. 4 is a cross-sectional view of FIG. 3 taken along the lines 4—4 and showing the construction of the material used for portions of the device of the present invention.

FIG. 5 is a view of a single piece of laminated material from which the pouch and integral flap of the present device are formed.

DETAILED DESCRIPTION OF THE INVENTION

Referring first to FIG. 1, one can see the device 1 of the present invention, in its preferred embodiment, as it might typically be used on a medical patient or person 2. As shown by FIGS. 1 and 2, a telemetry transmitter or other medical device 25 has been placed in pouch 3 which is secured about the person 2 by means of strap 4 and tab 5.

A telemetry transmitter is a small radio transmitter designed and constructed to be carried with a person and to transmit signals concerning the vital signs of the person received from sensors positioned at appropriate points on the body. As telemetry transmitters are well known in the art, they will not be further described. Other medical electronic equipment, such as temperature monitors, pulse and respiratory equipment and the like could also be inserted into pouch 3.

Wire leads 6 from the telemetry transmitter 25 located in pouch 3 are attached to sensors 7 which are placed at appropriate positions on the person 2, which positions might be as indicated in FIG. 1. Thus, signals from the body can be picked up by the sensors 7 and transmitted along the wire leads 6 to the telemetry transmitter located in pouch 3. From there the signals are preferably transmitted by the transmitter to appropriate receiving equipment for monitoring of the vital signs. Such receiving equipment may be centrally located and may be configured to display or record the received signal and to alert the appropriate personnel should a change in the patient's monitored vital sign indicate the need for prompt medical attention. Since such receiving equipment is also well known in the art, it will not be described further. The device 1 of the present invention allows a medical device, such as a telemetry transmitter, to be comfortably and securely mounted about the midsection of the person 2.

As can be seen in FIGS. 1, 2 and 3, the preferred embodiment of the present invention has a generally rectangular pouch 3 into which a medical device 25 may be placed through opening 15. The cutaway view, FIG. 2, illustrates the medical device 25 disposed within the pouch 3. Wire leads 6 are connected to the medical device 25 at 26 and traverse the wall of pouch 3 through slit 18. Flap 16, shown in the open position in FIG. 3 is folded over opening 15 of pouch 3 and attached thereto by the engagement of tab 17 with pouch 3 thereby securing the medical device in place within the pouch 3. A strap 4 connected to one end of pouch 3 can be extended around the midsection of a person and held in place by the engagement of strap 4 with tab 5, which is attached to the opposite end of pouch 3. Thus, the pouch 3 can be held securely in place about the midsection of person 2.

The detailed construction of the preferred embodiment is described with reference to FIGS. 3, 4 and 5. FIG. 4 is a cross-sectional view of a layer of the laminated material which, in the peferred embodiment, is used to fabricate both the strap 4 and the pouch 3 with its integral flap 16. The laminated material comprises a layer of spongy foam material 9 which is waterproof, to one side of which has been bonded a thin layer of cloth material 10 having a pile surface 27. The pouch 3 can be formed from a single piece 28 of the laminated material as shown in FIG. 5 by folding the piece 28 along a line 11 and by sewing through the then adjacent layers at edges 12 and 13, in such a manner that the layer of cloth material 10 forms the outside surface of pouch 3 and the layer of spongy foam material 9 forms the inside of the pouch 3. (Thus, the front 14 of the pouch 3, as seen in FIG. 3, has a cloth surface.) The resulting pouch 3 will then have an opening 15 and a flap 16. Extending outward from the tip of flap 16 and generally parallel to flap 16 is a flexible rectangular tab 17. Flap 16, which is formed by the extension on one side of the pouch 3 beyond the opening 15, is capable of being folded over the opening 15 and held in place over opening 15 through the engagement of tab 17 with the outside surface of the front 14 of pouch 3. The surface of tab 17 which engages the outside surface of the front 14 of pouch 3 when flap 16 is in the folded-over position consists of a plurality of extended short, stiff, hook-like fibers well known and generally referred to by the trademark Velcro. Such fibers, herein referred to as hook fibers, have the capacity of engaging certain cloth materials having pile surfaces and thereby fastening themselves to said cloth surfaces. Because these fibers are well known, they and their method of operation will not be discussed in detail herein. The other surface of tab 17 is smooth. The cloth material 10 which forms the outside surface of the front 14 of pouch 3 is a non-smooth, fibrous, cloth material having a pile surface suitable for engaging and fastening to the hook fibers of tab 17 when tab 17 is placed in contact with the outside surface of the front 14 of pouch 3. The pouch 3 also contains a slit 18 located in one side of the pouch. In the preferred embodiment this slit 18 is located in the front 14 of the pouch 3. The slit 18 serves as a passage for the wire leads 6 connecting the sensors 7 to the telemetry transmitter 25 as shown in FIGS. 1 and 2.

Extending outward from edge 12 of pouch 3 is a flexible rectangular tab 5. Tab 5 is similar in construction to tab 17 which has already been described, that is, one surface of tab 5 contains hook fibers while the other surface is smooth. Surface 20 of tab 5 as shown in FIG. 3 is the surface containing the hook fibers. A strap 4 is formed of laminated material, the construction of which is shown in FIG. 4 and has already been described. The strap 4 is attached at one of its ends to edge 13 of the pouch 3 such that the cloth surface 10 of strap 4 is toward the front 14 of pouch 3.

In operation, pouch 3 is positioned on the front surfae of person 2 such that when the pouch is opened, flap 16 of pouch 3 is on that side of the pouch closest to the person 2 and extends in an upward direction toward the head of person 2. The strap 4 is passed all the way around the midsection of person 2 such that surface 22 of strap 4 is in contact with the person 2. Strap 4 is then pulled tight about the midsection of person 2 in the back and side areas of the person 2. The fastening of the device to the person 2 is accomplished first by a movement in a generally horizontal plane of the pouch 3 away from the front surface of person 2 while maintaining a slight pulling tension between the pouch 3 and the end 23 of the attached strap 4 which now almost encircles the person 2. With the pouch 3 no longer placed in contact with the front surface of person 2, the remainder of strap 4 can be laid along its surface 22 against the midsection of the person 2 in the general area over which the pouch 3 was initially positioned. Holding the remainder of strap 4 in place, pouch 3 is rotated back toward its original position on the front surface of person 2 in such a manner that it now is placed adjacent to surface 24 of strap 4 and further such that tab 5 of pouch 3 is placed adjacent but not against surface 24. Before tab 5 is placed against surface 24 of the strap 4 a pulling force is exerted on it so that strap 4 and pouch 3 are both snug about the midsection of person 2. Surface 20 of tab 5 is then placed against surface 24 of the strap 4. The hook fibers on surface 20 of tab 5 engage the cloth material of surface 24 thereby holding the strap 4 and pouch 3 securely about the midsection of person 2. The sensors 7 may then be positioned on the person 2 and the telemetry transmitter 25 inserted into pouch 3 through opening 15. The wire leads 6, which connect the sensors 7 to the telemetry transmitter 25, are passed through the slit 18 and connected to the telemetry transmitter 25. Flap 16 is folded over opening 15 such that tab 17 is brought into contact with the surface of front 14 of pouch 3. The hook fibers located on tab 17 then engage the cloth material of surface 14 thereby securely fastening flap 16 over opening 15 to hold the telemetry transmitter within pouch 3, where it is protected from damage by the spongy foam material used to construct pouch 3. FIG. 1 shows the present invention as it might typically be used on a medical patient.

While the presently preferred embodiment has been described with respect to a specific configuration, other configurations are of course within the scope of the present invention. For example, tab 17 and tab 5 can have other than a rectangular configuration. Further, fasteners other than the Velcro-type described may be used both to secure the device about the midsection of the person 2 and to secure the flap 16 over the opening 15. In particular, a button may be sewed to the front of pouch 3 and a button hole placed near the tip of flap 16 in order to secure flap 16 over opening 15. It would also be possible to eliminate flap 16 altogether and use a zipper or hook fastening means along the opening 15. Rather then extend from edge 12 of pouch 3, tab 5 could be attached to the back surface of pouch 3. Thus many variations with regard to specific configurations are possible.

As another example of additional configurations possible, in place of slit 18, it may be desirable to route the wire leads 6 directly through opening 15.

Other configurations could use materials different from that used in the preferred embodiment. In the preferred embodiment, a spongy foam material and a cloth material having a pile surface are chosen such that the device can be easily and repeatedly washed. Obviously, many other materials and methods of construction would be suitable.

This invention, therefore, is not to be limited to the specific embodiments shown.

I claim:

1. A device for holding medical equipment about the midsection of a person comprising:
    a generally flat padded pouch of waterproof spongy foam material having an opening into which the medical equipment can be inserted said pouch having two opposing ends;
    closure means for said opening joined to said pouch;
    a long, narrow, flexible, soft strip which can be extended around the midsection of a person beneath the person's clothing, said strip formed of spongy foam material for placement against the person, said strip having a surface opposite that placed against the person at least partially covered by a pile material capable of engaging hook fibers, and being attached at one end to said pouch;
    a tab of material having a surface of hook fibers, said tab being attached to said pouch and serving to secure said strip about the midsection of a person through the engagement of said hook fibers on said tab with said pile material on said strip,
    whereby said medical equipment can be securely held in said pouch and said pouch can be securely and comfortably attached about the midsection of a person.

2. The device according to claim 1 in which said strip is attached to one end of said pouch and said tab is attached to the opposite end of said pouch.

3. The device according to claims 1 or 2 wherein said closure means comprises a foldable flap.

4. The device according to claims 1 or 2 wherein said device is made entirely of washable materials.

5. The device according to claim 4 further comprising a small second opening located in a side of said pouch through which wire leads may be routed, said wire leads connecting sensors placed on the body to medical equipment placed in said pouch.

6. A device for holding medical equipment or the like about the midsection of a person comprising:
- a washable pouch fabricated from a piece of waterproof, spongy foam material having a bottom, a top, opposing sides, and opposing ends adjacent to said opposing sides and said top and bottom, with a first opening at said top and an integral securable flap joined to said pouch adjacent to said top, said flap being closable and securable over said opening;
- a long, narrow, flexible, washable strip attached to said pouch at one of said opposing ends, said strip being fabricated from a piece of spongy foam material to which has been bonded on one side a fibrous cloth material having a pile surface suitable for engaging hook fibers, said strip placed for placement around the midsection of a person beneath the person's clothing with the spongy foam side of the strip against the midsection of the person;
- a washable tab of material, one surface of which contains hook fibers, said tab being attached along at least one of its edges to the said opposing end of said pouch opposite to said end at which said strip is attached, said tab for engaging said pile surface when said strip is placed around the midsection of a person;
- whereby medical equipment or the like may be securely held in said pouch and said pouch may be securely and comfortably attached about the midsection of a person.

7. The device according to claim 6 further comprising a small second opening located in a side of said pouch through which wire leads may be routed.

8. A device for holding a telemetry transmitter attachable by wires to sensors placeable on the body of a patient said device comprising:
- a pouch having an integral closable flap dimensioned to hold said transmitter and consisting of a unitary panel of material having parallel ends and a width therebetween dimensioned to be slightly larger than the length of said transmitter and a height dimensioned to be larger than twice the width of said transmitter, said panel being folded over along a line joining and perpendicular to its parallel ends to form folded over portions of said panel said folded over portions of said panel being fastened along their overlapping parallel ends so as to form a pouch portion having a first opening with an extending flap portion foldable over said first opening to cover a telemetry transmitter placed within said pouch, said material forming said unitary panel consisting of two coextensive, laminated layers, the first layer being waterproof spongy foam material and the second layer being a pile material, said panel being folded so that said spongy foam layer forms the interior of said pouch;
- a first tab having a surface having hook fibers, said tab adjacent the end of said flap so as to engage any portion of the outer pile layer of the pouch when the flap is folded over said pouch to cover a telemetry transmitter placed therein;
- a slit formed in said panel in said pouch portion situated near one end thereof for passage therethrough of the wires connecting said sensors to said transmitter;
- a belt portion consisting of an elongated web of the same material as said panel, one end of said web being attached to one end of said panel along the pouch portion thereof, such that the spongy foam layer of said web faces in a direction toward the side of the panel from which the flap portion extends from the pouch portion for contact with the body of the patient; and
- a second tab having a surface having hook fibers, said second tab attached to the other end of said panel along the pouch portion thereof such that said surface faces in a direction toward the side of the panel from which the flap portion extends from the pouch portion so as to engage the pile layer of the web when said belt portion is belted around the patient, said web being of substantial length to circumvent the midsection of a patient of substantial girth, the second tab being engagable with the pile layer of said web at any place along the web so as to accommodate patients having a wide range of girths.

* * * * *